(12) United States Patent
Kim et al.

(10) Patent No.: US 11,031,345 B2
(45) Date of Patent: Jun. 8, 2021

(54) INTEGRATED CIRCUIT PACKAGE AND METHOD OF FORMING SAME

(71) Applicant: Medtronic, Inc., Minneapolis, MN (US)

(72) Inventors: Chunho Kim, Phoenix, AZ (US);
Mark R. Boone, Gilbert, AZ (US);
Randolph E. Crutchfield, Scottsdale, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 16/536,633

(22) Filed: Aug. 9, 2019

(65) Prior Publication Data

US 2020/0058592 A1     Feb. 20, 2020

Related U.S. Application Data

(60) Provisional application No. 62/718,631, filed on Aug. 14, 2018.

(51) Int. Cl.
*H01L 23/538* (2006.01)
*H01L 23/31* (2006.01)
(Continued)

(52) U.S. Cl.
CPC ...... *H01L 23/5389* (2013.01); *H01L 21/4853* (2013.01); *H01L 21/4857* (2013.01);
(Continued)

(58) Field of Classification Search
CPC ............. H01L 23/5389; H01L 21/4853; H01L 21/4857; H01L 21/565; H01L 23/3128;
(Continued)

(56) References Cited

U.S. PATENT DOCUMENTS 6,084,297 A    7/2000  Brooks et al.
6,506,632 B1   1/2003  Cheng et al.
(Continued)

OTHER PUBLICATIONS (PCT/US2019/046248) PCT Notification of Transmittal of the International Search Report and the Written Opinion of the International Searching Authority, dated Nov. 12, 2019, 13 pages.

*Primary Examiner* — Victor A Mandala
(74) *Attorney, Agent, or Firm* — Mueting Raasch Group (57) ABSTRACT

Various embodiments of an integrated circuit package and a method of forming such package are disclosed. The package includes a substrate having a core layer disposed between a first dielectric layer and a second dielectric layer, a die disposed in a cavity of the core layer, and an encapsulant disposed in the cavity between the die and a sidewall of the cavity. The package further includes a first patterned conductive layer disposed within the first dielectric layer, a device disposed on an outer surface of the first dielectric layer such that the first patterned conductive layer is between the device and the core layer, a second patterned conductive layer disposed within the second dielectric layer, and a conductive pad disposed on an outer surface of the second dielectric layer such that the second patterned conductive layer is between the conductive pad and the core layer.

12 Claims, 5 Drawing Sheets

(51) Int. Cl.
*H01L 23/58* (2006.01)
*H01L 23/00* (2006.01)
*H01L 21/48* (2006.01)
*H01L 21/56* (2006.01)

(52) U.S. Cl.
CPC ........ *H01L 21/565* (2013.01); *H01L 23/3128* (2013.01); *H01L 23/5383* (2013.01); *H01L 23/5386* (2013.01); *H01L 23/585* (2013.01); *H01L 24/19* (2013.01); *H01L 24/20* (2013.01); *H01L 2224/214* (2013.01); *H01L 2924/1203* (2013.01); *H01L 2924/1205* (2013.01); *H01L 2924/1207* (2013.01); *H01L 2924/1301* (2013.01); *H01L 2924/1305* (2013.01); *H01L 2924/1306* (2013.01); *H01L 2924/13026* (2013.01); *H01L 2924/13055* (2013.01); *H01L 2924/13091* (2013.01)

(58) Field of Classification Search
CPC ............. H01L 23/5383; H01L 23/5386; H01L 23/585; H01L 24/19; H01L 24/20; H01L 2224/214; H01L 2924/1203; H01L 2924/1205; H01L 2924/1207; H01L 2924/1301; H01L 2924/13026; H01L 2924/1305; H01L 2924/13055; H01L 2924/1306; H01L 2924/13091; H01L 24/25; H01L 24/92; H01L 2224/06181; H01L 24/06; H01L 24/73; H01L 2224/82001; H01L 2224/2518; H01L 25/16; H01L 23/62; H01L 2224/73267; H01L 2224/32225; H01L 24/24; H01L 24/82; H01L 2224/92244; H01L 2924/15311; H01L 2224/16227; H01L 21/486; H01L 23/49827; H01L 23/49844; H01L 23/5384; H01L 23/15; H01L 2224/18; H01L 2221/68345; H01L 21/6835; H05K 1/185; A61N 1/375

See application file for complete search history.

(56) References Cited

U.S. PATENT DOCUMENTS

| | | | |
|---|---|---|---|
| 6,731,002 | B2 * | 5/2004 | Choi .................... H01L 23/3735 257/692 |
| 8,664,756 | B2 | 3/2014 | Boone et al. |
| 2008/0315372 | A1 | 12/2008 | Kuan et al. |
| 2010/0289126 | A1 | 11/2010 | Pagaila et al. |
| 2011/0074047 | A1 | 3/2011 | Pendse |
| 2011/0169150 | A1 | 7/2011 | Su et al. |
| 2014/0077361 | A1 | 3/2014 | Lin et al. |
| 2016/0099213 | A1 * | 4/2016 | Tae ......................... H01L 24/82 257/777 |
| 2016/0148873 | A1 * | 5/2016 | Chiang ................... H01L 24/20 257/774 |
| 2016/0247781 | A1 * | 8/2016 | Sung ....................... H01L 24/19 |
| 2016/0284657 | A1 | 9/2016 | Han et al. |
| 2017/0033027 | A1 | 2/2017 | Chen et al. |
| 2017/0140202 | A1 * | 5/2017 | Huang ............... G06K 9/00053 |
| 2018/0235544 | A1 * | 8/2018 | Nagarkar ............... B33Y 80/00 |
| 2018/0337160 | A1 * | 11/2018 | Drab ....................... H01L 24/81 |
| 2018/0366403 | A1 * | 12/2018 | Yu ........................ H01L 23/5389 |
| 2019/0058241 | A1 * | 2/2019 | So .......................... H01L 23/66 |
| 2019/0131224 | A1 * | 5/2019 | Choi .................... H01L 23/3128 |

\* cited by examiner

INTEGRATED CIRCUIT PACKAGE AND METHOD OF FORMING SAME

CROSS-REFERENCE TO RELATED APPLICATIONS

This application claims the benefit of U.S. Provisional Application Ser. No. 62/718,631, filed Aug. 14, 2018, the entire content of which is incorporated herein by reference.

BACKGROUND

A wide variety of electronic assemblies such as those that are utilized for implantable medical devices (IMDs) employ electronic circuitry, e.g., for providing electrical stimulation of body tissue and/or monitoring a physiologic condition. Such IMDs may deliver electrical therapy energy in the form of shocking energy and stimulating pulses to selected body tissue. These IMDs typically include output circuitry for generating the electrical energy under prescribed conditions and at least one lead bearing a stimulation electrode for delivering the electrical energy to the selected tissue. For example, cardiac pacemakers and implantable cardioverter-defibrillators (ICDs) have been developed for maintaining a desired heart rate during episodes of bradycardia or for applying cardioversion or defibrillation therapies to the heart upon detection of serious arrhythmias. Other nerve, brain, muscle, and organ tissue stimulating medical devices are also known for treating a variety of conditions.

Currently available IMDs, including ICDs and implantable pulse generators (IPGs), typically include a metallic housing that is hermetically sealed and, therefore, is impervious to body fluids, and a header or connector assembly mounted to the housing for making electrical and mechanical connection with one or more leads. Such devices also possess telemetry capabilities for communicating with external devices. Over the past several years, IMDs have evolved from relatively bulky devices to complex miniaturized devices that exhibit increasing functionality. For example, numerous improvements have been made in cardioversion/defibrillation leads and electrodes that have enabled the cardioversion/defibrillation energy to be precisely delivered to selected one or more portions of upper and lower heart chambers, thereby dramatically reducing the delivered shock energy required to cardiovert or defibrillate the heart chamber. High voltage output circuitry has also been improved to provide monophasic, biphasic, or multi-phase cardioversion/defibrillation shock or pulse waveforms, sometimes with particular combinations of cardioversion/defibrillation electrodes, that are efficacious in lowering the required shock energy to cardiovert or defibrillate the heart.

The miniaturization of IMDs is driving size and cost reduction of all IMD components, including the electronic circuitry components, where it is desirable to increase the density and reduce the size of such components so that the overall circuitry can be more compact. As the dimensions of IMDs decrease, the electronic circuits of the IMD are formed as integrated circuits to fit within a minimal space. Furthermore, as the dimensions of the components are also being reduced, it is desirable to improve the use of the dimensions within the IMD package.

One response to this desire has been through technological improvements to the packaging for the devices in which the output circuitry is included through such packaging techniques as reconstituted wafer packaging. In particular, development efforts in reconstituted wafer packaging, also known as fan out wafer level packaging, focus on producing thinner and smaller electronic packages.

SUMMARY

In general, the present disclosure provides various embodiments of an integrated circuit package and a method of forming such package. The integrated circuit package can include a substrate having a core layer disposed between a first dielectric layer and a second dielectric layer, a die disposed in a cavity of the core layer, and an encapsulant disposed in the cavity between the die and a sidewall of the cavity. The package can also include a first patterned conductive layer disposed within the first dielectric layer and a device disposed on an outer surface of the first dielectric layer such that the first patterned conductive layer is between the device and the core layer, where the device is electrically connected to the die. The package can also include a second patterned conductive layer disposed within the second dielectric layer and a conductive pad disposed on an outer surface of the second dielectric layer such that the second patterned conductive layer is between the conductive pad and the core layer, where the conductive pad is electrically connected to the die.

In one aspect, the present disclosure provides an integrated circuit package that includes a substrate having a core layer disposed between a first dielectric layer and a second dielectric layer, a die disposed in a cavity of the core layer, and an encapsulant disposed in the cavity between the die and a sidewall of the cavity. The integrated circuit package further includes a first patterned conductive layer disposed within the first dielectric layer; a device disposed on an outer surface of the first dielectric layer such that the first patterned conductive layer is between the device and the core layer, where the device is electrically connected to the die; a second patterned conductive layer disposed within the second dielectric layer; and a conductive pad disposed on an outer surface of the second dielectric layer such that the second patterned conductive layer is between the conductive pad and the core layer. The conductive pad is electrically connected to the die.

In another aspect, the present disclosure provides a method of forming an integrated circuit package. The method includes disposing a cavity in a core layer, disposing a carrier layer on the core layer over the cavity, and disposing a die within the cavity on the carrier layer. The method further includes disposing a first dielectric layer on the core layer over the cavity such that the core layer is between the first dielectric layer and the carrier layer, where the first dielectric layer includes a first patterned conductive layer disposed between first and second sublayers of the first dielectric layer, and where the first patterned conductive layer includes a field plate that is spaced apart from the die; removing the carrier layer from the core layer; and disposing a second dielectric layer on the core layer such that the core layer is between the first and second dielectric layers. The second dielectric layer includes a second patterned conductive layer disposed between first and second sublayers of the second dielectric layer.

All headings provided herein are for the convenience of the reader and should not be used to limit the meaning of any text that follows the heading, unless so specified.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

In this application, terms such as "a," "an," and "the" are not intended to refer to only a singular entity but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The phrases "at least one of" and "comprises at least one of" followed by a list refers to any one of the items in the list and any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

Also herein, the recitations of numerical ranges by endpoints include all numbers subsumed within that range as well as the endpoints (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

Throughout the specification, reference is made to the appended drawings, where like reference numerals designate like elements, and wherein:

FIGS. 3A-I are various cross-section views of one embodiment of forming an integrated circuit package, where

DETAILED DESCRIPTION

In general, the present disclosure provides various embodiments of an integrated circuit package and a method of forming such package. The integrated circuit package can include a substrate having a core layer disposed between a first dielectric layer and a second dielectric layer, a die disposed in a cavity of the core layer, and an encapsulant disposed in the cavity between the die and a sidewall of the cavity. The package can also include a first patterned conductive layer disposed within the first dielectric layer and a device disposed on an outer surface of the first dielectric layer such that the first patterned conductive layer is between the device and the core layer, where the device is electrically connected to the die. The package can also include a second patterned conductive layer disposed within the second dielectric layer and a conductive pad disposed on an outer surface of the second dielectric layer such that the second patterned conductive layer is between the conductive pad and the core layer, where the conductive pad is electrically connected to the die.

Microelectronic elements, such as semiconductor chips or dies, are typically flat bodies with electrical connection contacts disposed on an exterior surface, where the electrical connection contacts are connected to the internal electrical circuitry of the element itself. Microelectronic elements are oftentimes packaged to form integrated circuit packages, or assemblies, having a surface that is surface mountable with terminals that electrically connect to the element's internal contacts. The package or assembly may then be connected to test equipment to determine whether the packaged device conforms to a desired performance standard. Once tested, the package may be connected to a larger circuit, e.g., a circuit in an electronic product such as an implantable medical device. The package or assembly for such microelectronic elements may include the integrated circuit packages described herein.

One or more embodiments of integrated circuit packages may provide one or more benefits over existing packages. For example, disposing one or more dies in a cavity disposed in a core layer of an integrated circuit package can provide a reduction in size (i.e., height) of the package over currently existing packages. Further, wire bonds may not be required to connect the die to a patterned conductive layer of the package as the die can be a flip-chip die that is electrically connected by one or more die contacts disposed on a top or bottom surface of the die when the die is disposed within the cavity of the core layer. Various embodiments of methods for forming such packages described herein can also provide for packaging of numerous dies and other components in one process flow, thereby reducing the costs of manufacturing these integrated circuit packages. In one or more embodiments, a parasitic inductance of an interconnect to the die of the package can be lower than that produced by wire bonds. This can allow the die to operate at a higher frequency and can also reduce inductive voltage spikes when switching high current. Further, the overall resistance of one or more embodiments of packages described herein can exhibit reduced resistive losses and increased current capability. Further, one or more packages described herein can include multiple contacts of a die to be distributed over source and drain pads of the package. Such configurations can decrease current density in the die, increase maximum current capability, and reduce power loss. Such configurations can also allow heat to be drawn from the die through two or more sides of the package. Further, one or more embodiments of packages described herein can allow components and integrated circuit packages to be stacked upon one another to form a three-dimensional high-voltage stack structure.

The core layer can include any suitable material or materials. In one or more embodiments, the core layer can be a glass core layer. Such glass core layers can be manufactured using any suitable technique or techniques. A glass core layer can provide improved dielectric properties over other types of materials (e.g., silicon) that could be utilized for the core layer. Such improved dielectric properties can allow for one or more conductive layers to be disposed directly on the core layer without requiring first disposing a dielectric layer be disposed between the core layer and the patterned conductive layer. Further, one or more embodiments of glass core layers can exhibit improved warpage resistance.

Figure 1:
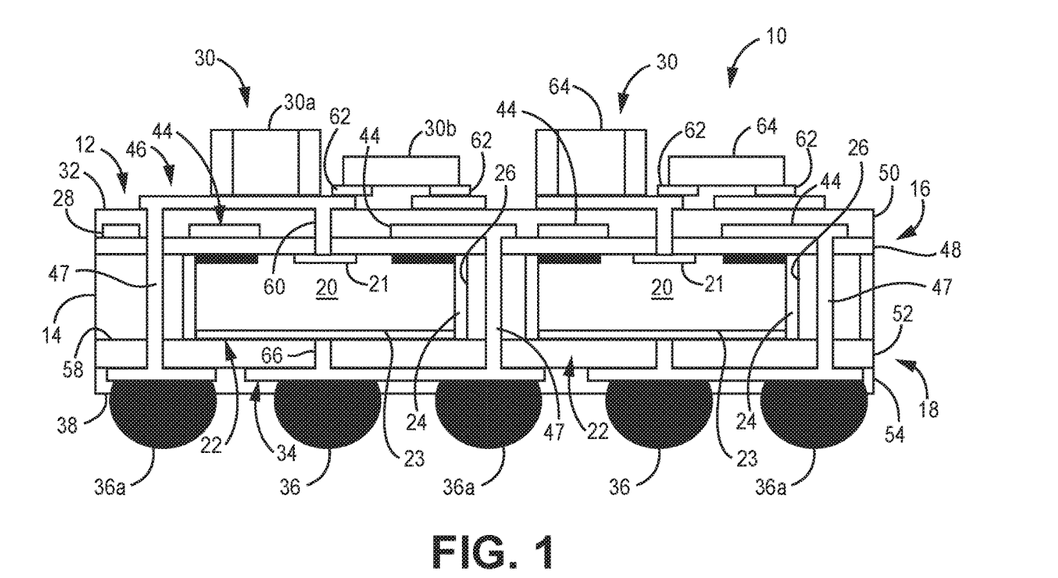
FIG. 1 is a schematic cross-section view of one embodiment of an integrated circuit package.
Figure 2:
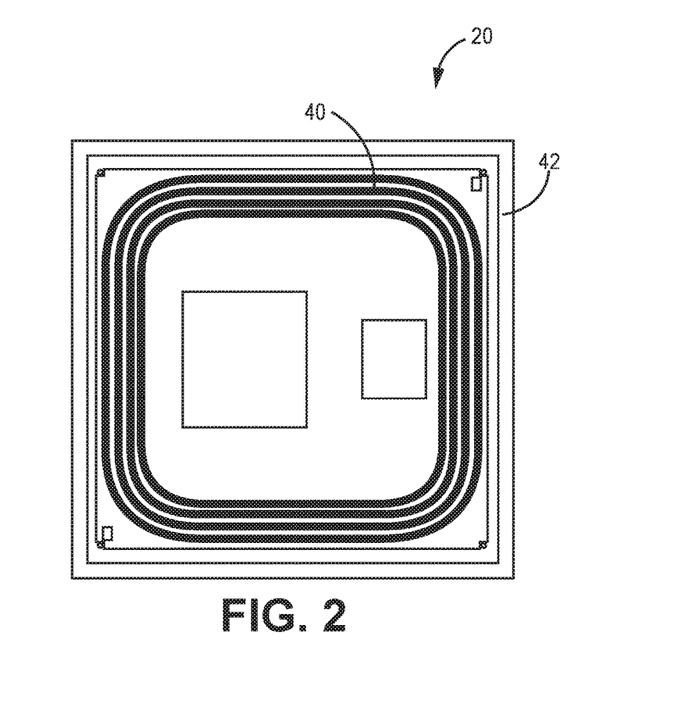
FIG. 2 is a schematic top view of a major surface of a die of the integrated circuit package of FIG. 1.

FIGS. 1-2 are various views of one embodiment of an integrated circuit package 10. The integrated circuit package 10 includes a substrate 12 having a core layer 14 disposed between a first dielectric layer 16 and a second dielectric layer 18. One or more dies 20 are each disposed in a cavity 22 of the core layer 14. Further, an encapsulant 24 is disposed in each cavity 22 between the respective die 20 and a sidewall 26 of the cavity. The package 10 also includes a first patterned conductive layer 28 disposed within the first dielectric layer 16. One or more devices 30 are disposed on an outer surface 32 of the first dielectric layer 16 such that the first patterned conductive layer 28 is between the one or more devices and the core layer 14. One or more of the devices 30 are electrically connected to one or more of the dies 20. The package 10 also includes a second patterned conductive layer 34 disposed within the second dielectric layer 18. In one or more embodiments, one or more conductive pads 36 can be disposed on or in an outer surface 38 of the second dielectric layer 18 such that the second patterned conductive layer 34 is between the conductive pads and the core layer 14. Further, in one or more embodiments, one or more of the conductive pads 36 can be electrically connected to one or more of the dies 20 using any suitable technique or techniques as is further described herein.

The substrate 12 can include any suitable substrate. Further, the substrate 12 can include any suitable material or materials, e.g., metallic, polymeric, or inorganic materials and combinations thereof. In one or more embodiments, the substrate 12 can be a nonconductive or dielectric substrate that provides electrical isolation between various conductors, vias, dies, etc. For convenience and without intending to be limiting, FIG. 1 depicts the substrate 12 as a monolithic (i.e., single) layer. In one or more embodiments, the substrate 12 can include any suitable number of layers, where the layers can be formed from the same or different materials. Further, the substrate 12 can have any suitable dimensions. For example, the substrate 12 can have any suitable thickness as measured in a direction orthogonal to the outer surface 32 of the first dielectric layer 16. Further, the substrate 12 can be formed using any suitable technique or techniques.

In one or more embodiments, the substrate 12 includes the core layer 14 disposed between the first dielectric layer 16 and the second dielectric layer 18. The core layer 14 can include any suitable material or materials, e.g., the same materials described herein regarding the substrate 12. In one or more embodiments, the core layer 14 can include one or more of glass, quartz, sapphire, FR4 (flame retardant 4), ceramic, etc. In one or more embodiments, the core layer 14 provides the entirety of the substrate 12. Further, in one or more embodiments, one or more additional layers can be disposed on the core layer 14 to form the substrate 12. For example, in one or more embodiments, one or more pattern conductive layers (not shown) can be disposed on one or both surfaces of the core layer 14 to provide the substrate 12.

The core layer 14 can include one or more cavities 22. The cavities 22 can be formed in the core layer 14 using any suitable technique or techniques. In one or more embodiments, one or more cavities 22 can extend completely through the core layer 14. Further, in one or more embodiments, a depth or height of one or more cavities 22 as measured in a direction orthogonal to the outer surface 32 of the first dielectric layer 16 can be less than a thickness of the core layer so that the such cavities do not extend through the core layer 14. Each cavity 22 can take any suitable shape or shapes in a plane parallel to the outer surface 32 of the first dielectric layer 16, e.g., elliptical, rectangular, polygonal, etc.

Each cavity 22 includes one or more sidewalls 24. Each sidewall 24 can take any suitable shape or shapes in a plane orthogonal to the outer surface 32 of the first dielectric layer 16 (i.e., in the plane of FIG. 1). In one or more embodiments, the sidewalls 24 can have a flat surface that is orthogonal to the outer surface 32 of the first dielectric layer 16. In one or more embodiments, one or more sidewalls 24 can take a tapered shape such that a cross-sectional area of the cavity 22 changes in a direction orthogonal to the outer surface 32 of the first dielectric layer 16. Further, in one or more embodiments, one or more sidewalls 24 can include one or more curved portions.

The cavities 24 can have any suitable dimensions. In one or more embodiments, at least one cavity 24 can have a width in a direction parallel to the outer surface 32 of the first dielectric layer 16 that is greater than a width of the die 20 disposed in the cavity. In one or more embodiments, a cavity 24 can have a width that is equal to a width of the die 20 disposed therein such that the die is in contact with one or more portions of the sidewall 24 of the cavity.

The first and second dielectric layers 16, 18 can include any suitable material or materials, e.g., polyimide, bismaleimide triazine, polybenzoxazole, photoresist, glass, quartz, sapphire, etc. In one or more embodiments, at least one of the first and second dielectric layers 16, 18 includes an electrically insulative material. Further, the first and second dielectric layers 16, 18 can have any suitable dimensions. In one or more embodiments, at least one of the first and second dielectric layers 16, 18 can include two or more layers or sublayers, and each sublayer can include the same or different materials. For example, the first dielectric layer 16 includes a first sublayer 48 and a second sublayer 50. Further, the second dielectric layer 18 includes a first sublayer 52 and a second sublayer 54. The first and second sublayers 48, 50 of the first dielectric layer 16 can be disposed together using any suitable technique or techniques. In one or more embodiments, the first and second sublayers 48, 50 can be laminated together to form the first dielectric layer 16. Similarly, the first and second sublayers 52, 54 of the second dielectric layer 18 can be disposed together using any suitable technique or techniques. In one or more embodiments, the first and second sublayers 52, 54 can be laminated together to form the second dielectric layer 18. Although depicted as each including two sublayers, the first and second dielectric layers 16, 18 can each include any suitable number of sublayers.

The first and second dielectric layers 16, 18 can be formed using any suitable technique or techniques. In one or more embodiments, at least one of the first and second dielectric layers 16, 18 can be formed on the substrate 12. In one or more embodiments, at least one of the first and second dielectric layers 16, 18 can be formed separately and then connected to the substrate 12, e.g., by laminating one or both of the first and second dielectric layers to the substrate.

As mentioned herein, the integrated circuit package 10 can include one or more dies 20. Further, the package 10 can include any suitable number of dies 20 disposed in any suitable arrangement or array. In one or more embodiments, one or more dies 20 can be disposed in a cavity 22 of the core layer 14. Although depicted as including one die 20 per cavity 22, in one or more embodiments, two or more dies can be disposed within a single cavity. In one or more embodiments, one or more dies 20 can be disposed in a cavity 22 such that the die is completely within the cavity. For example, each die 20 can have a die height measured in a direction orthogonal to the outer surface 32 of the first dielectric layer 16 that is no greater than a height of the cavity 22 within which the die is disposed. In one or more embodiments, the die height of one or more dies 20 can be greater than the height of the cavity 22 within which the respective die is disposed.

The package 10 can include any suitable type of die or dies 20. In one or more embodiments, the package 10 can include one or more high-voltage dies that can be utilized, e.g., in an implantable medical device (see, e.g., implantable medical device 200 of FIG. 4). As used herein, the term "high-voltage die" refers to an electronic component or device that is operable with a potential greater than about 50 V across any two electrical terminals or contacts of the component. Such high-voltage components may be further operable at DC voltages greater than about 100 V, and even further may be operable at DC voltages greater than about 500 V, 1000 V, 1600 V, 3000 V and even greater, perhaps in the tens of thousands or more volts. In one or more embodiments, the package 10 can include one or more low-voltage dies. In one or more embodiments, the one or more dies 20 can include one or more field effect transistors (FETs), metal oxide semiconductors (MOS), MOSFETs, insulated gate bipolar junction transistors (IGBT), thyristors, bipolar transistors, diodes, MOS-controlled thyristors, resistors, capacitors, etc. Although the dies 20 of FIG. 1 are illustrated as being on the same plane, in one or more embodiments, the dies may be arranged in a stacked relationship.

In one or more embodiments, one or more dies 20 can include a field termination structure 40 (FIG. 2) disposed on a major surface 42 of the die. In one or more embodiments, the major surface 42 faces a field plate 44 (FIG. 1) that can be electrically connected to at least one of the first patterned conductive layer 28, the second patterned conductive layer 34, and a conductive pad 36 disposed on or in the outer surface 38 of the second dielectric layer 18 as is further described herein.

The field termination structure 40 can include any suitable conductor or conductors manufactured using any suitable material or materials. Further, the field termination structure 40 can include any suitable structure that is adapted to at least in part control propagation of electric fields within the die 20 to mitigate or prevent avalanche breakdowns. For example, in one or more embodiments, the field termination structure 40 can include a mesa-type structure. Such breakdowns can occur when a critical electric field for the material (e.g., silicon) of the die is exceeded. In one or more embodiments, the field termination structure 40 can include one or more floating P-type rings in an N-type substrate. The P-type rings can occupy volume at the outer surface 42 of the die 20 and can cause the depletion region in the N-type material of the die to spread out farther across the surface of the die where the electric field can be at its greatest. A volume occupied by these P-type rings can force the depletion region in the N-type substrate of the die 20 to spread out over a larger area and distance at the outer surface 42 and within the die (because charge balance is required to be maintained for a main reverse-biased P-N junction). These P-type rings can be spaced in a way to provide a relatively consistent electric field across the surface 42 and within the die 20. As shown in FIG. 2, the field termination structure 40 can include one or more rings that can be disposed in any suitable shape or pattern on the outer surface 42 of the die 20.

The dies 20 can be electrically connected to at least one of the first patterned conductive layer 28, the second patterned conductive layer 34, a third patterned conductive layer 46, and one or more conductive pads 36 using any suitable technique or techniques. In one or more embodiments, one or more vias 60 can be disposed through the first sublayer 48 of the first dielectric layer 16 to electrically connect one or more top contacts 21 of the die 20 to the first patterned conductive layer 28. Further, in one or more embodiments, one or more vias 66 can be disposed through the first sublayer 52 of the second dielectric layer 18 to electrically connect one or more bottom contacts 23 of the die 20 to the second patterned conductive layer 34.

Also disposed within one or more cavities 22 of the core layer 14 is the encapsulant 24. Encapsulant 24 can be disposed in any suitable portion or portions of the cavity 22. In one or more embodiments, the encapsulant 24 is disposed in the cavity 22 between the die 20 and one or more portions of the sidewall 26 of the cavity. The encapsulant 24 can include any suitable material or materials, e.g., UV curing type or heat curing type encapsulating materials, such as BCB, polybenzo-bisoxazole, epoxy, photoresist, and epoxy resins such as the SINR3170, siloxane resin, manufactured by Shin-Etsu Chemical Co., Ltd., Japan, R4507 EMC (epoxy mold compound) manufactured by Nagase, G730 EMC manufactured by Sumitomo, etc. Any suitable technique or techniques can be utilized to dispose the encapsulant 24 within the cavity. In one or more embodiments, a portion of the first dielectric layer 16 can form the encapsulant 24 as is further described herein. The encapsulant 24 can be adapted to at least partially encapsulate the die 20 within the cavity 22 such that the die remains in the cavity.

As mentioned herein, the encapsulant 24 can be disposed in the cavity 22 between the die 20 and the sidewall 26 of the cavity using any suitable technique or techniques. In one or more embodiments, the encapsulant 24 can include a portion of the first dielectric layer 16. For example, the die 20 can be disposed within the cavity 22, and the first dielectric layer 16 can be disposed on the core layer 14 (or substrate 12) by, e.g., laminating the first dielectric layer to the core layer. During the lamination process, a portion of the first dielectric layer 16 can flow into the cavity 22 between the die 20 and the sidewall 26 of the cavity such that the portion at least partially encapsulates the die within the cavity. In one or more embodiments where the first dielectric layer 16 includes sublayers, a portion or portions of the first sublayer 48 that is disposed on the core layer (or substrate 12) can flow into the cavity 22 to form the encapsulant 24.

Disposed within the first dielectric layer 16 is the first patterned conductive layer 28. The first dielectric layer 16 can include any suitable number of patterned conductive layers disposed on or within the first dielectric layer. In one or more embodiments, the first dielectric layer 16 can include the third patterned conductive layer 46 disposed on the outer surface 32 of the first dielectric layer 16. Further, the first and third patterned conductive layers 28, 46 can include any suitable type of conductive layer or layers, e.g., one or more redistribution layers. The first and third patterned conductive layers 28, 46 can be electrically connected to additional patterned conductive layers, devices, conductive pads, etc. using one or more conductive vias 47 that are disposed within the first dielectric layer 16. The first and third patterned conductive layers 28, 46 can include any suitable conductive material or materials and be formed using any suitable technique or techniques as is further described herein. Further, the first and third patterned conductive layers 28, 46 can be disposed within or on the first dielectric layer 16 using any suitable technique or techniques.

The first patterned conductive layer 28 can be disposed in any suitable location within the first dielectric layer 16. In one or more embodiments, the first patterned conductive layer 28 can be disposed between the first and second sublayers 48, 50 of the first dielectric layer 16.

Further, the second patterned conductive layer 34 is disposed within the second dielectric layer 18. The second patterned conductive layer 34 can include any suitable patterned conductive layer, e.g., the same patterned conductive layer described regarding the first patterned conductive layer 28. The second dielectric layer 18 can include any suitable number of patterned conductive layers disposed within or on the second dielectric layer. In one or more embodiments, the second patterned conductive layer 34 can be disposed between the first and second sublayers 52, 54 of the second dielectric layer 18. The second patterned conductive layer 34 can be electrically connected to at least one of the dies 20 by via 66, the first patterned conductive layer 28 by vias 47, the third patterned conductive layer 46 by vias 47, and one or more conductive pads 36.

Disposed on the outer surface 32 of the first dielectric layer 16 are one or more devices 30. The integrated circuit package 10 can include any suitable number of devices 30. Further, the integrated circuit package 10 can include any suitable devices, e.g., at least one of a capacitor, resistor, passive integrated capacitor system, logic circuit, analog circuit, etc. The one or more devices 30 can be disposed on the outer surface 32 of the first dielectric layer 16 such that the first patterned conductive layer 28 is between the devices and the core layer 14.

One or more of the devices 30 can be electrically connected to one or more of the dies 20 using any suitable technique or techniques. For example, in the embodiment illustrated in FIG. 1, a first device 30a and a second device 30b are electrically connected to the die 20 by the third patterned conductive layer 46 and via 60 that is disposed through the first dielectric layer 16. The devices 30a, 30b can be electrically connected to the third patterned conductive layer 46 using any suitable technique or techniques. In one or more embodiments, one or more device contacts 62 of a device 30 can be electrically connected to the third patterned conductive layer 46. The device contacts 62 can be disposed in any suitable location relative to the third patterned conductive layer 46. For example, in one or more embodiments, the device contacts 62 can be disposed between a device 30 and the third patterned conductive layer 46. In one or more embodiments, one or more device contacts 62 can be disposed on a top surface 64 of the device 30 and wire bonded to the third patterned conductive layer 46 (not shown).

Disposed on the outer surface 54 of the second dielectric layer 18 are one or more conductive pads 36. The conductive pads 36 can be disposed in any suitable location on or in the second dielectric layer 18. Further, the integrated circuit package 10 can include any suitable number of conductive pads 36. The conductive pads 36 can include any suitable type of electrical connector, e.g., solder balls, solder, bumps, copper pillars, copper pillars with solder caps, conductive polymers, compliant interconnects, etc. In one or more embodiments, the conductive pads 36 are disposed such that the second patterned conductive layer 34 is between the conductive pads and the core layer 14. Further, in one or more embodiments, one or more conductive pads 36 are electrically connected to one or more dies 30. For example, as illustrated in FIG. 1, conductive pad 36 is electrically connected to die 20 by the via 66 that extends from the second patterned conductive layer 34 to the die. In one or more embodiments, one or more conductive pads 36 can be electrically connected to at least one of the second patterned conductive layer 34, one or more dies 20, the first patterned conductive layer 28, the third patterned conductive layer 46, and one or more devices 30. Further, in one or more embodiments, one or more conductive pads 36 can be electrically connected to one or more field plates 44 using any suitable technique or techniques.

The field plates 44 can be disposed on or within the integrated circuit package 10 in any suitable location. In the embodiment illustrated in FIG. 1, the field plates 44 are disposed within the first dielectric layer 16 such that one or more of the field plates are spaced apart from one or more of the dies 20. The field plates 44 can include a portion of the first patterned conductive layer 28 or be separate from the first patterned conductive layer. In one or more embodiments, one or more of the field plates 44 can be formed simultaneously with the first patterned conductive layer 28. The field plates 44 can include any suitable field plates, e.g., the field plates described in U.S. Pat. No. 8,664,756 to Boone et al.; entitled RECONSTITUTED WAFER PACKAGE WITH HIGH VOLTAGE DISCRETE ACTIVE DICE AND INTEGRATED FIELD PLATE FOR HIGH TEMPERATURE LEAKAGE CURRENT STABILITY.

In one or more embodiments, the field plate 44 is spaced from die 20 at an optimal spacing gap that is large enough to prevent dielectric breakdown of the insulator but close enough to set up a strong enough field to dominate the system. The optimal distance for the spacing gap may be determined based on the characteristics of the dielectric material of first dielectric layer 16 and the test and/or operating conditions for the die 20. In one or more embodiments, the characteristics that are taken into account may include the operating conditions of package 10, including such things as the operating voltage and temperature regarding the breakdown characteristics for the dielectric material of the first dielectric layer 16. In one or more embodiments, the distance of the spacing gap between field plate 44 and the die 20 may alternatively or in addition be determined based on the dielectric strength of the material used for formation of the first dielectric layer 16. In one or more embodiments, this spacing gap can be at least approximately 25 µm to no greater than approximately 300 µm depending on the operating and/or test parameters for a given component. The controlling factor in the design and selection of a spacing gap is that the field plate 44 will be effective up to the maximum breakdown strength of the die 20 to prevent field effect leakage at room temperature and higher temperatures. As an example, a 1000 V MOSFET intended to operate at 80 percent rated voltage at 125° C. can have field plate 44 spaced apart at a distance in the range of 50 to 200 μm from the field termination structure 40. As another example, a spacing of approximately 50 μm to approximately 75 μm can prevent dielectric breakdown and ensure current stability for a die to be operated at 80 percent of its rated 1600 V and up to 150° C. during a high temperature leakage current test. As a result, for a given dielectric material, the higher the voltage rating of the component or die the greater the spacing gap between the die 20 and field plate 44 is required to prevent dielectric breakdown and ensure leakage current stability and eliminate or substantially prevent field effect leakage at room temperature. Further, positioning the field plate 44 within the first dielectric layer 16 can permit the dimensions of the individual conductive pads 36 to be determined independently of the spacing requirements for the field plate 44.

In one or more embodiments, at least a portion of the field plate 44 overlaps the field termination structure 40 of the die 20 in a direction orthogonal to the outer surface 32 of the first dielectric layer 16. In one or more embodiments, the field plate 44 substantially overlaps the field termination structure 40, i.e., a majority of a surface area of the field plate overlaps with a majority of a surface area of the field termination structure. As an illustration of the embodiments, the proportion including a majority may be 51%, or 75% or 85% or 98% or any variants within those percentages. In one or more embodiments, the surface area of the field plate 44 may extend beyond the surface area of the field termination structure 40. In one or more embodiments, the field plate 44 may be dimensioned to be substantially co-extensive with a surface area of the front-side face of the die 20. In one or more embodiments, the dimensions of field plate 44 can be determined based on the planar surface area of the field termination structure 40. As such, field plate 44 has a surface area that is at least the size of the surface area of field termination structure 40. In one or more embodiments, if there is a plurality of concentric field termination structures 40, field plate 44 can either be formed in a corresponding plurality of separate field plates each having a surface area of its respective field termination structure or as a single field plate with a surface area approximating that of the total annular ring that includes the concentric termination rings. In embodiments where the surface area of field plate 44 is dimensioned based on the size of the field termination structure 40, the field plate surface area may be coextensive with the surface area of field termination structure and/or may extend beyond the surface area of field termination structure. Additionally, the field plate 44 is aligned with or positioned directly above or in generally the same vertical plane as the field termination structure 40.

In one or more embodiments, the field plate 44 can be adapted to receive a biasing voltage to produce an electric field between die 20 and the field plate. The biasing voltage can have a magnitude at least as great as the magnitude of the biasing voltage applied to die 20, where the voltages have the same polarity. For example, for a package 10 with an N-type substrate, a positive biasing voltage is applied to field plate 44, and the positive biasing voltage can have a magnitude at least as great as the magnitude of the most positive biasing voltage applied to die 20. Similarly, for a package 10 having a p-type substrate, a negative biasing voltage is applied to field plate 44, and the negative biasing voltage can have a magnitude at least as great as the magnitude of the most negative biasing voltage applied to die 20. The field plate 44 can be connected directly to a terminal of die 20 if the component has unidirectional blocking characteristics, such as MOSFETs and diodes. In one or more embodiments where the die 20 has bidirectional blocking, such as a thyristor, the voltage on field plate 44 can be switched. In either case, field plate 44 is biased with a polarity that promotes accumulation of majority carriers at the surface of the lightly doped surface region at the field termination structure 40.

The field plate 44 can be electrically connected to one or more second conductive pads 36a that are disposed on the outer surface 38 of the second dielectric layer 18. The field plate 44 can be connected to the second conductive pads 36a using any suitable technique or techniques. In one or more embodiments, the field plate 44 can be electrically connected to the second conductive pads 36a by vias 47 that extend between the first dielectric layer 16 and the second dielectric layer 18.

Figure 5:
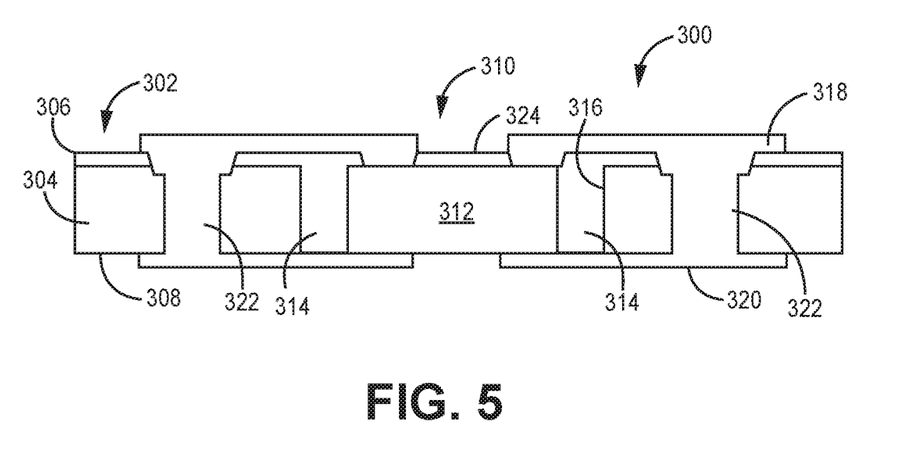
FIG. 5 is a schematic cross-section view of another embodiment of an integrated circuit package.

As mentioned herein, one or more embodiments of integrated circuit packages can include a glass core layer. For example, FIG. 5 is a schematic cross-section view of another embodiment of an integrated circuit package 300. All of the design considerations and possibilities regarding the integrated circuit package 10 of FIGS. 1-2 apply equally to the integrated circuit package 300 of FIG. 5.

The package 300 includes a substrate 302 including a glass core layer 304 that includes a first major surface 306, a second major surface 308, and a cavity 310 disposed between the first major surface and the second major surface of the glass core layer. The package 300 further includes a die 312 disposed in the cavity 310 of the glass core layer 304, and an encapsulant 314 disposed in the cavity between the die and a sidewall 316 of the cavity. A first patterned conductive layer 318 can be disposed adjacent the first major surface 306 of the glass core layer 304. As used herein, the term "adjacent the first major surface" means that an element or component is disposed closer to the first major surface 306 of the glass core layer 304 than to the second major surface 308 of the glass core layer. The package 300 further includes a second patterned conductive layer 320 disposed adjacent the second major surface 308 of the glass core layer 304. As used herein, the term "adjacent the second major surface" means that an element or component is disposed closer to the second major surface 308 of the glass core layer 304 than to the first major surface 306 of the glass core layer. The package 300 also includes one or more conductive vias 322 disposed in the glass core layer 304 that extend between the first and second major surfaces 306, 308 of the glass core layer. In one or more embodiments, the conductive vias 322 can be electrically connected to at least one of the first and second patterned conductive layers 318, 320. Further, the die 312 is electrically connected to at least one of the first and second patterned conductive layers 318, 320 using any suitable technique or techniques. In one or more embodiments, the die 312 is electrically connected to each of the first and second patterned conductive layers 318, 320.

In one or more embodiments, the package 300 can include one or more devices (not shown) disposed on at least one of the first and second patterned conductive layers 318, 320. Such device or devices can include any suitable device, e.g., device 30 of package 10 of FIG. 1. The device or devices can be electrically connected to at least one of the first and second patterned conductive layers 318, 320 using any suitable technique or techniques.

Disposed adjacent the first major surface 306 of the glass core layer 304 is the first patterned conductive layer 318. In one or more embodiments, the first patterned conductive layer 318 can be disposed directly on the first major surface 306 of the glass core layer 304. In one or more embodiments, a dielectric layer 324 can be disposed between the first patterned conductive layer 318 and the first major surface 306 of the glass core layer 304. The dielectric layer 324 can include any suitable dielectric layer or layers, e.g., first dielectric layer 16 of package 10 of FIG. 1. The dielectric layer 324 can be disposed on the first major surface 306 of the glass core layer 304 using any suitable technique or techniques, e.g., the dielectric layer can be laminated to the glass core layer.

Further, the second patterned conductive layer 320 can be disposed directly on the second major surface 318 of the glass core layer 304. In one or more embodiments, a second dielectric layer (e.g., second dielectric layer 18 of package 10) can be disposed between the second patterned conductive layer 320 and the second major surface 308 of the glass core layer 304. The second dielectric layer 320 can be disposed on the second major surface 308 of the glass core layer 304 using any suitable technique or techniques, e.g., the second dielectric layer can be laminated to the glass core layer.

Disposed between the die 312 and the sidewall 316 of the cavity 310 is the encapsulant 314. The encapsulant 314 can include any suitable material or materials that are adapted to encapsulate the die, e.g., the same material or materials described herein regarding encapsulant 24 of package 10 of FIG. 1. In one or more embodiments, the encapsulant 314 can include a portion or portions of the dielectric layer 324 as described herein regarding first dielectric layer 16 of package 10.

The die 312 disposed within the cavity 310 of the glass core layer 304 can include any suitable device or circuit, e.g., the same devices or circuits described herein regarding die 20 of package 10. In one or more embodiments, the die 312 can include a high-voltage electrical component. In one or more embodiments, the die 312 can include a low-voltage component.

Any suitable technique or techniques can be utilized to form the integrated circuit package 10 of FIGS. 1-2 and the integrated circuit package 300 of FIG. 5. For example, FIGS. 3A-I are various schematic cross-section views of one embodiment of a method 100 of forming the integrated circuit package 10. Although described in reference to the integrated circuit package 10 of FIGS. 1-2, the method 100 can be utilized to form any suitable integrated circuit package. Further, the method 100 is illustrated as including one die 20; however, the method can be utilized to form integrated circuit packages that include two or more dies. In one or more embodiments, the method 100 can be utilized to form two or more integrated circuit packages 10 simultaneously utilizing one or more wafers.

Figure 3A:
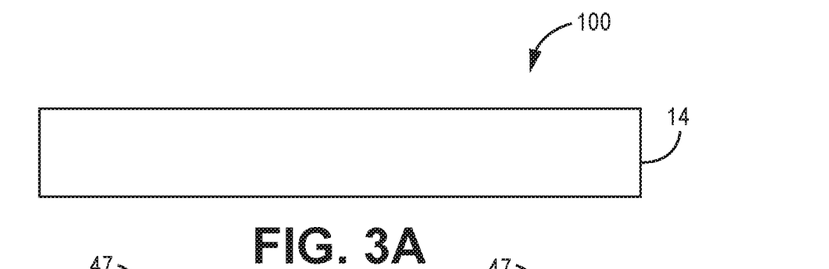
FIG. 3A is a schematic cross-section view of a core layer.
Figure 3B:
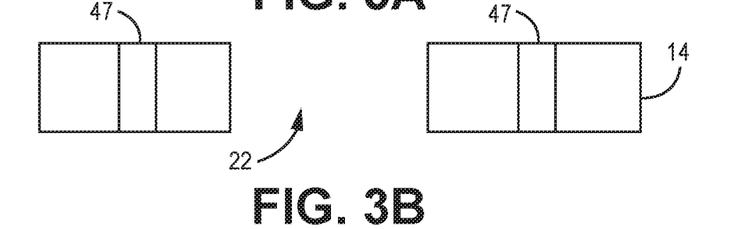
FIG. 3B is a schematic cross-section view of a cavity disposed in the core layer.

In FIG. 3A, the core layer 14 is provided. In one or more embodiments, one or more additional layers can be disposed on one or both major surfaces of the core layer 14 to provide the substrate 12. One or more cavities 22 can be formed in the core layer 14 as shown in FIG. 3B using any suitable technique or techniques, e.g., drilling, laser drilling, chemical etching, plasma etching, stamping, etc. Further, one or more vias 47 can be formed using any suitable technique or techniques. For example, in one or more embodiments, an opening can be formed using any suitable technique or techniques, and a conductive material can be disposed within the opening to form the conductive via 47. In one or more embodiments, the vias 47 can be formed after the patterned conductive layers 28, 34, 46 (if included) have been formed.

Figure 3C:
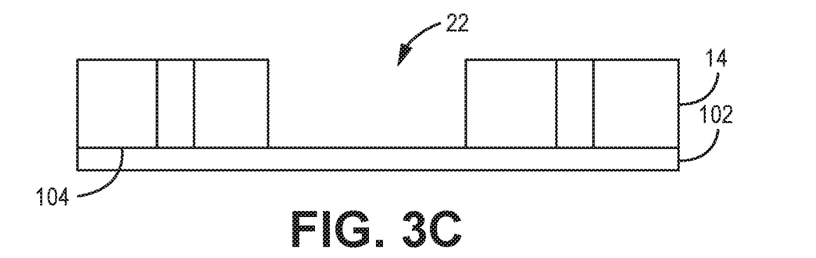
FIG. 3C is a schematic cross-section view of a carrier disposed on the core layer.

In FIG. 3C, a carrier layer 102 can be disposed on a bottom surface 104 of the core layer 14 and over the cavity 22. The carrier layer 102 can include any suitable carrier or transport. In one or more embodiments, a suitable release layer (not shown) can be disposed between the carrier layer 102 and the bottom surface 104 of the core layer 14. Further, an optional glass layer (not shown) can be disposed on the carrier layer 102 such that the carrier layer is between the optional glass layer and the core layer 14. Such optional glass layer can provide additional support to the core layer 14 during processing of the integrated circuit package 10.

Figure 3D:
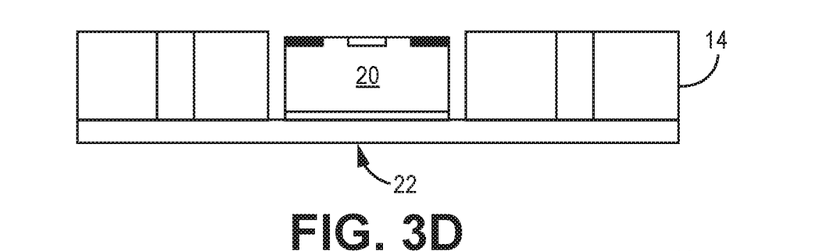
FIG. 3D is a schematic cross-section view of a die disposed in the cavity of the core layer.

The die 20 can be disposed within the cavity 22 in FIG. 3D using any suitable technique or techniques. In embodiments where the cavity 22 extends completely through the core layer 14, the die 20 can be placed directly onto the carrier layer 102 or a release layer disposed on the carrier layer.

Figure 3E:
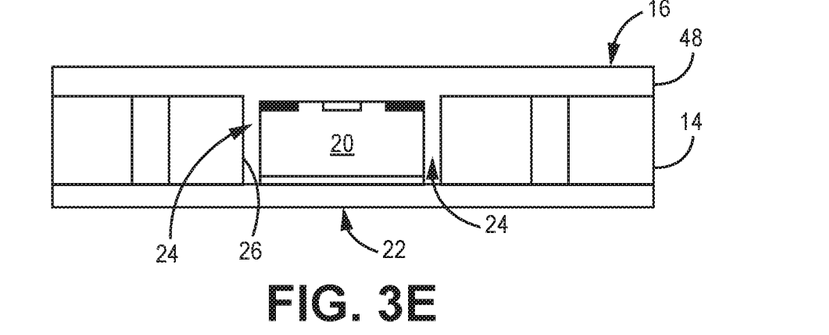
FIG. 3E is a schematic cross-section view of a first dielectric layer disposed on the core layer over the cavity.

In FIG. 3E, the first dielectric layer 16 can be disposed on the core layer 14 and over the cavity 22 such that the core layer is between the first dielectric layer 16 and the carrier layer 102 using any suitable technique or techniques. In embodiments where the first dielectric layer 16 includes sublayers, the first sublayer 48 can be disposed on the core layer 16 as shown in FIG. 3E. In one or more embodiments, the first sublayer 48 of the first dielectric layer 16 can be disposed on the core layer 14 such that a portion or portions of the first sublayer flows into the cavity to provide encapsulant 24 between the sidewall 26 of the cavity and the die 20. In one or more embodiments, the first dielectric layer 16 (or the first sublayer 48 of the first dielectric layer) can be laminated to the core layer 14.

Figure 3F:
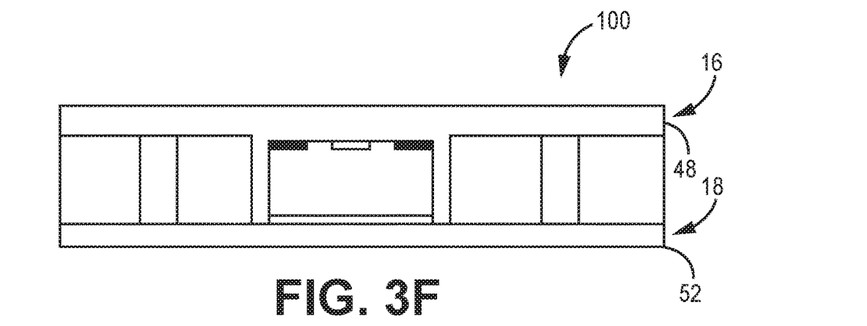
FIG. 3F is a schematic cross-section view of the carrier removed from the core layer and a second dielectric layer disposed on the core layer.

The carrier layer 102 can be removed as shown in FIG. 3F using any suitable technique or techniques. Further, the second dielectric layer 18 can be disposed on the core layer 14 using any suitable technique or techniques, e.g., the second dielectric layer or sublayers of the second dielectric layer can be laminated onto the core layer. In embodiments where the second dielectric layer 18 includes two or more sublayers, the first sublayer 52 can be disposed on the core layer 14.

Figure 3G:
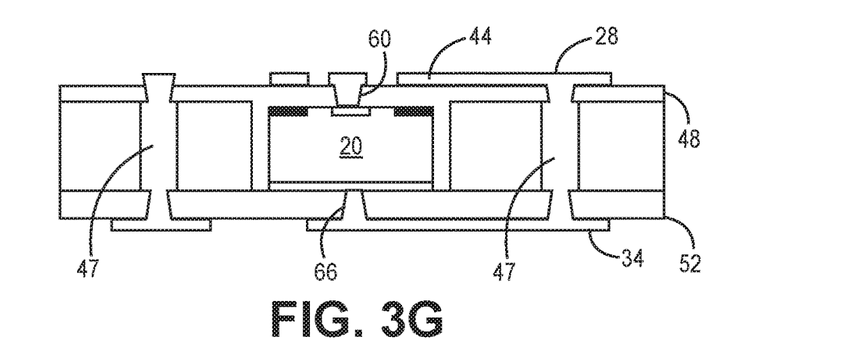
FIG. 3G is a schematic cross-section view of a field plate disposed within the first dielectric layer and a patterned conductive layer on an outer surface of the second dielectric layer.

In FIG. 3G, the first patterned conductive layer 28 can be disposed on or within the first sublayer 48 of the first dielectric layer 16 using any suitable technique or techniques. For example, in one or more embodiments, a continuous conductive layer can be disposed on the first sublayer 48, and the continuous conductive layer can then be patterned using any suitable technique or techniques, e.g., photoresist application, photolithography, electroless plating, electroplating, chemical etching, dry etching, physical vapor deposition, etc. In one or more embodiments, the field plate 44 can be disposed within the first dielectric layer 16 using any suitable technique or techniques such that the field plate is spaced apart from the die 20. In one or more embodiments, the first patterned conductive layer 28 can include the field plate 44.

Further, the second patterned conductive layer 34 can be disposed on the first sublayer 52 of the second dielectric layer 18 using any suitable technique or techniques, e.g., the same techniques utilized to form the first patterned conductive layer 28. Prior to formation of the first and second patterned conductive layers 28, 34, one or more vias 60 can be disposed through the first sublayer 48 such that the first patterned conductive layer 28 is electrically connected to the die 20. Further, one or more vias 66 can be formed through the first sublayer 52 of the second dielectric layer 18 such that the second patterned conductive layer 34 is electrically connected to the die 20. Any suitable technique or techniques can be utilized to form the vias 60, 66. Further, vias 47 can be extended through the first sublayer 48 of the first dielectric layer 16 and electrically connected to the first patterned conductive layer 28 using any suitable technique or techniques. Vias 47 can also be extended through the first sublayer 52 of the second dielectric layer 18 using any suitable technique or techniques.

Figure 3H:
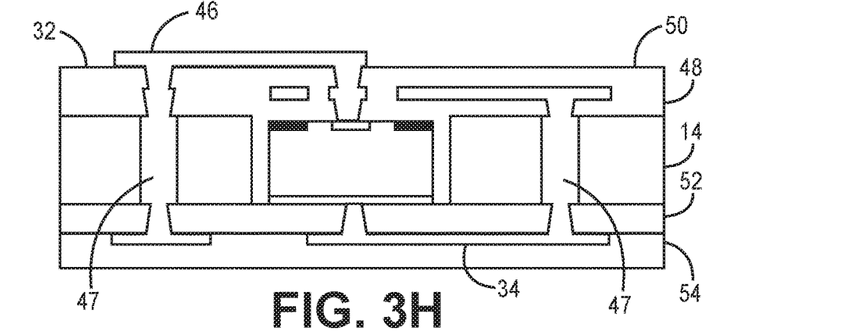
FIG. 3H is a schematic cross-section view of a patterned conductive layer disposed on an outer surface of the first dielectric layer.

In FIG. 3H, the second sublayer 50 of the first dielectric layer 16 can be disposed on the first patterned conductive layer 28 and the first sublayer 48 using any suitable technique or techniques. In one or more embodiments, the second sublayer 50 can be disposed over the entire first patterned conductive layer 28. The third patterned conductive layer 46 can be disposed on the second sublayer 50 using any suitable technique or techniques, e.g., the same techniques utilized to form the first patterned conductive layer 28. Further, via 60 can be extended through the first dielectric layer 16 between the outer surface 32 of the first dielectric layer and the die 20 using any suitable technique or techniques such that the die is electrically connected to the third patterned conductive layer 46. In one or more embodiments, via 47 can be extended through the second sublayer 40 of the first dielectric layer 16 such that the third patterned conductive layer 46 is electrically connected to the first and second patterned conductive layers 28, 34.

Further, as shown in FIG. 3H, the second sublayer 54 of the second dielectric layer 18 can be disposed on the first sublayer 52 of the second dielectric layer using any suitable technique or techniques. The second sublayer 54 can be disposed over one or more portions of the second patterned conductive layer 34 and the first sublayer 52 of the second dielectric layer 18. In one or more embodiments, the integrated circuit package 10 does not include the second sublayer 54.

Figure 3I:
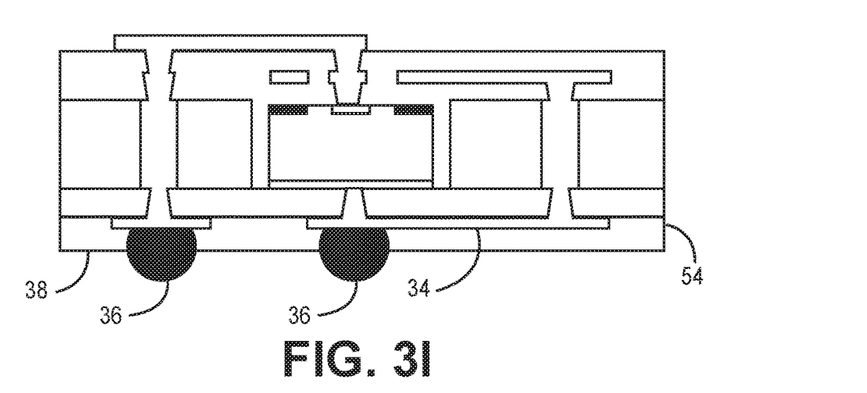
FIG. 3I is a schematic cross-section view of conductive pads disposed on an outer surface of the second dielectric layer.

In FIG. 3I, one or more conductive pads 36 can be disposed on or in the second dielectric layer 18 using any suitable technique or techniques. In one or more embodiments, one or more of the conductive pads 36 can be electrically connected to at least one of the first patterned conductive layer 28, the die 20, the second patterned conductive layer 34, the third patterned conductive layer 46 and one or more devices 30 (FIG. 1). Although illustrated as being disposed at least partially within the second sublayer 54, the conductive pads 36 can be disposed on the outer surface 38 of the second sublayer.

Figure 4:
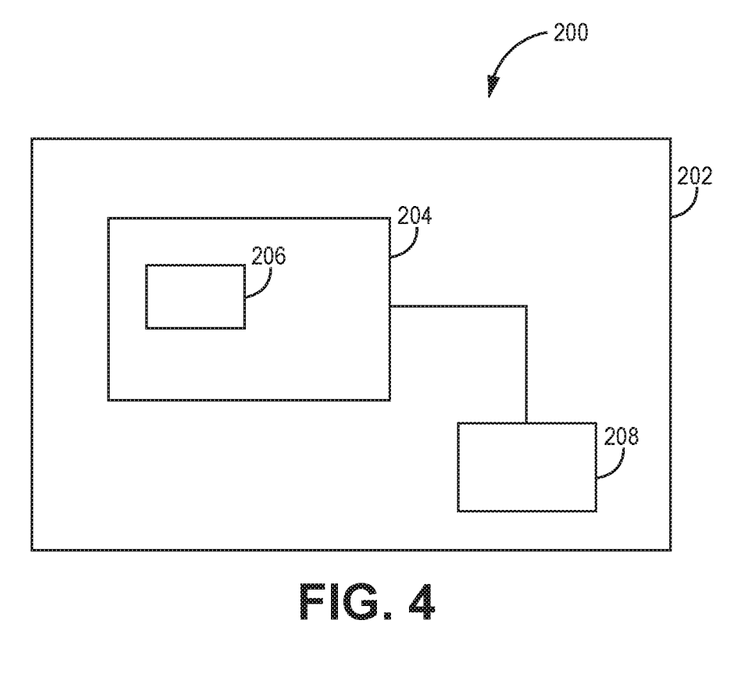
FIG. 4 is as schematic plan view of one embodiment of an implantable medical device that includes an integrated circuit package.

The various embodiments of integrated circuit packages described herein can be utilized in any suitable electronic system. For example, one or more embodiments of integrated circuit packages described herein can be utilized in an IMD, ICD, IPG, insertable cardiac monitor, implantable diagnostic monitor, deep brain stimulator, implantable neurostimulator, injectable neurostimulator, implantable ventricular assist device, etc. FIG. 4 is a schematic plan view of one embodiment of an implantable medical device (IMD) 200. The IMD 200 includes a housing 202 and electronic components 204 disposed within the housing. The electronic components 204 can include any suitable electronic devices, e.g., at least one of a capacitor, resistor, passive integrated capacitor system, logic circuit, analog circuit, crystal, accelerometer, RF circuit, antenna, transformer, connector, etc. In one or more embodiments, the electronic components 204 include an integrated circuit package 206. The package 206 can include any suitable integrated circuit package, e.g., integrated circuit package 10 of FIGS. 1-2 and package 300 of FIG. 5. The integrated circuit package 206 can be electrically connected to other electronic components 204 using any suitable technique or techniques. Also disposed within the housing 202 of the IMD is a power source 208 that is electrically connected to the electronic components using any suitable technique or techniques. The power source can include any suitable power source or combination of power sources, e.g., e.g., one or more batteries, capacitors, inductive-coupled energy devices, photovoltaic devices, betavoltaic devices, alphavoltaic devices, and thermo-electric devices.

All references and publications cited herein are expressly incorporated herein by reference in their entirety into this disclosure, except to the extent they may directly contradict this disclosure. Illustrative embodiments of this disclosure are discussed, and reference has been made to possible variations within the scope of this disclosure. These and other variations and modifications in the disclosure will be apparent to those skilled in the art without departing from the scope of the disclosure, and it should be understood that this disclosure is not limited to the illustrative embodiments set forth herein. Accordingly, the disclosure is to be limited only by the claims provided below.

What is claimed is:

1. An integrated circuit package, comprising:
   a substrate comprising a core layer disposed between a first dielectric layer and a second dielectric layer;
   a die disposed in a cavity of the core layer;
   an encapsulant disposed in the cavity between the die and a sidewall of the cavity;
   a first patterned conductive layer disposed within the first dielectric layer;
   a device disposed on an outer surface of the first dielectric layer such that the first patterned conductive layer is between the device and the core layer, wherein the device is electrically connected to the die;
   a second patterned conductive layer disposed within the second dielectric layer; and
   a conductive pad disposed on an outer surface of the second dielectric layer such that the second patterned conductive layer is between the conductive pad and the core layer, wherein the conductive pad is electrically connected to the die; and
   a field plate disposed within the first dielectric layer, wherein the field plate is spaced apart from the die.

2. The package of claim 1, wherein the field plate is electrically connected to a second conductive pad disposed on the outer surface of the second dielectric layer.

3. The package of claim 1, wherein the die further comprises a field termination structure disposed on an outer surface of the die that faces the field plate, wherein at least a portion of the field plate overlaps the field termination structure in a direction orthogonal to the outer surface of the first dielectric layer.

4. The package of claim 1, wherein the first and second dielectric layers are laminated to the substrate.

5. The package of claim 1, wherein the encapsulant comprises a portion of the first dielectric layer.

6. The package of claim 1, wherein the die comprises a high voltage electrical component.

7. The package of claim 6, wherein the high voltage electrical component is operable with a potential of at least 500 volts.

8. The package of claim 1, wherein the die comprises at least one of a field effect transistor, a metal oxide semiconductor field effect transistor, an insulated gate bipolar junction transistor, a thyristor, a bipolar transistor, a diode, a MOS-controlled thyristor, a resistor, and a capacitor.

9. The package of claim 1, wherein each of the first and second dielectric layers comprises two or more sublayers that are laminated together.

10. The package of claim 9, wherein the first patterned conductive layer is disposed between two sublayers of the first dielectric layer.

11. The package of claim 9, wherein the second patterned conductive layer is disposed between two sublayers of the second dielectric layer.

12. An implantable medical device comprising the integrated circuit package of claim 1.

* * * * *